(12) United States Patent
Campbell et al.

(10) Patent No.: US 6,225,620 B1
(45) Date of Patent: May 1, 2001

(54) PEACH PIT DETECTION APPARATUS AND METHOD

(75) Inventors: Duncan B. Campbell, Central Point, OR (US); James Ewan, Los Altos, CA (US); Cliff J. Leidecker, Rogue River; H. Parks Squyres, Medford, both of OR (US)

(73) Assignee: Key Technology, Inc., Walla Walla, WA (US)

( * ) Notice: Subject to any disclaimer, the term of this patent is extended or adjusted under 35 U.S.C. 154(b) by 0 days.

(21) Appl. No.: 09/277,568

(22) Filed: Mar. 26, 1999

Related U.S. Application Data
(60) Provisional application No. 60/080,106, filed on Mar. 31, 1998.

(51) Int. Cl.[7] .................................................. B07C 5/342
(52) U.S. Cl. .................. 250/221; 250/222.1; 250/223 R; 209/557
(58) Field of Search ...................................... 209/576, 577, 209/580, 581, 582; 250/221, 222.1, 223 R

(56) References Cited

U.S. PATENT DOCUMENTS

| | | |
|---|---|---|
| 4,146,135 * | 3/1979 | Sarkar et al. ......................... 209/580 |
| 4,186,836 | 2/1980 | Wassmer et al. ..................... 209/565 |
| 5,315,384 | 5/1994 | Heffington et al. ..................... 348/93 |
| 5,440,127 | 8/1995 | Squyres .............................. 250/341.8 |
| 5,464,981 | 11/1995 | Squyres et al. ................... 250/341.8 |
| 5,791,497 | 8/1998 | Campbell et al. .................... 209/577 |
| 5,808,305 | 9/1998 | Leidecker et al. ................ 250/341.8 |

* cited by examiner

Primary Examiner—F. L. Evans
(74) Attorney, Agent, or Firm—Wells, St. John, Roberts, Gregory & Matkin, P.S.

(57) ABSTRACT

A peach sorting system (110) conveys peaches (114) on a conveyor belt (112) past an inspection zone (126) that is lighted by an illumination source (90) radiating a number of emission peaks over visible and infrared portions of the spectrum. The illumination source generates the radiation from an Indium Iodide lamp (92) that is reflected off a parabolic reflector (94) and through a "soda straw" collimator (100) to illuminated the peaches. A detector system (118) employs line scanning visible and infrared cameras (142, 140) to sense visible and IR wavelength reflectance value differences existing between peach meat (124) and peach pit or pit fragments (126). Because there is a reversal in the reflectance values between the visible and infrared wavelengths, a data subtraction technique (150) is employed to enhance the detection contrast ratio. The data subtraction technique also cancels "glint" caused by specular reflections of the illumination source off the peaches and into the cameras.

20 Claims, 11 Drawing Sheets

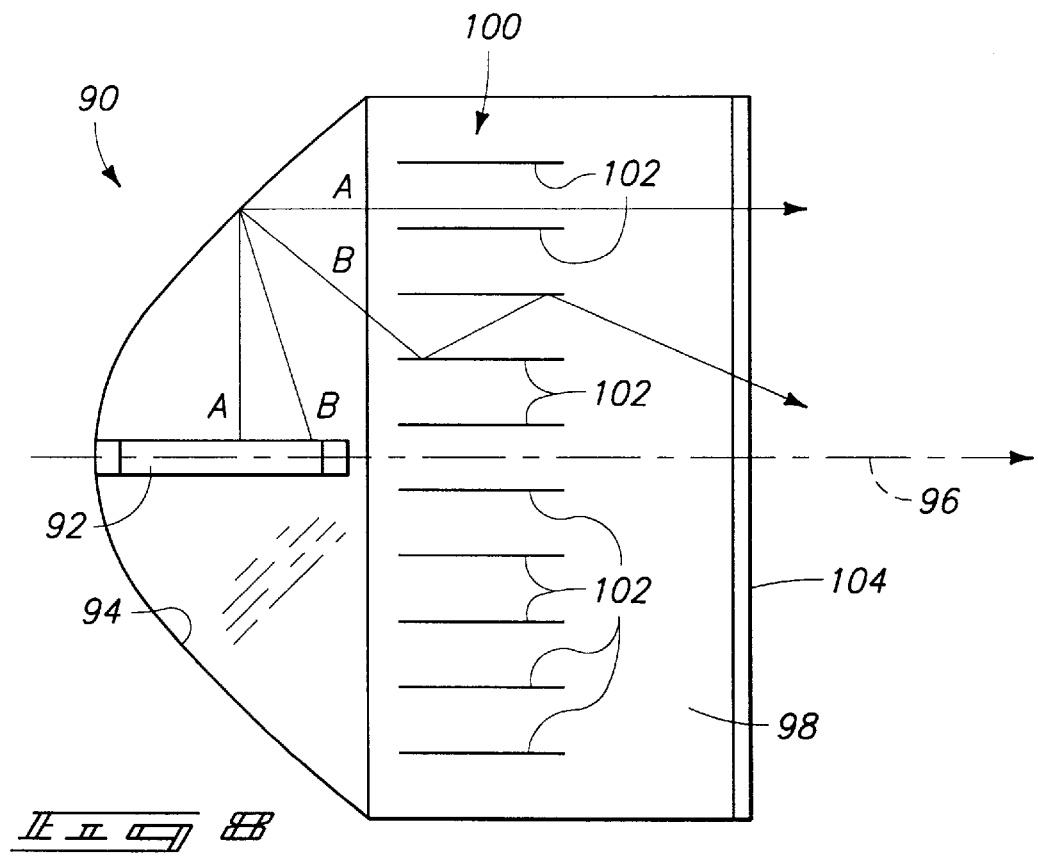
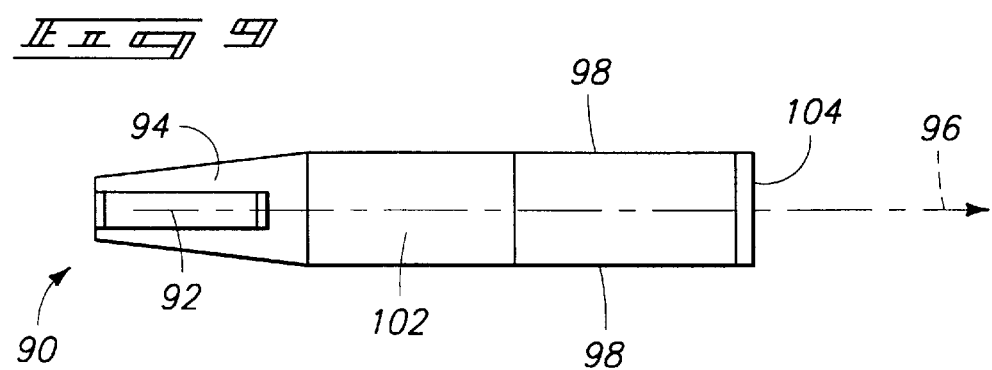

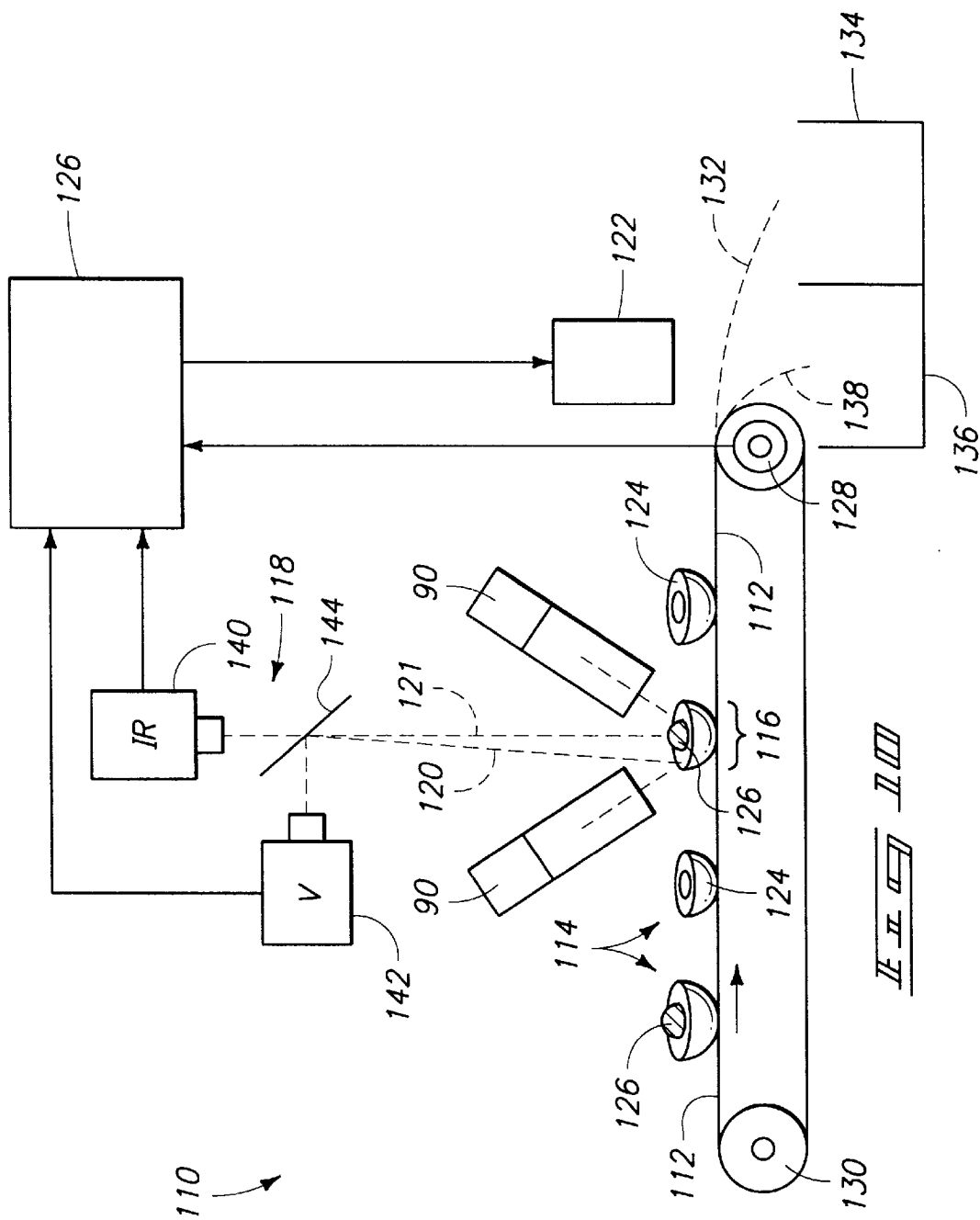

PEACH PIT DETECTION APPARATUS AND METHOD

RELATED APPLICATION

This application claims priority from U.S. Provisional Application No. 60/080,106, filed Mar. 31, 1998, for PEACH PIT DETECTION APPARATUS AND METHOD.

TECHNICAL FIELD

This invention relates to agricultural product inspection and more particularly to an apparatus and a method of inspecting peach halves for pits and pit fragments.

BACKGROUND OF THE INVENTION

A popular agricultural product is canned peach halves, slices and cubes. The peach variety typically used for canning is referred to as a "cling" peach, whereas the popular eating peach variety is referred to as "the free stone" peach, which is not used for canning because they lose their taste during the canning process. The variety names cling and free stone imply the relative ease with which the stone (hereafter "pit") can be removed from the fruit.

Many peach processors employ an Atlas splitting machine to remove the pit. This machine consist of a circumferential knife, that looks and functions much like the iris of a camera lens. As the blades of the machine close down on the peach, it cuts through the flesh until it meets the hard core of the pit. Once the pit is secured firmly in place by means of the blade, two cups approach from either side to grab the two peach halves. When the cups are in place they are rotated in opposite directions to twist the peach halves apart and separate them from the secured pit. Unfortunately, the blade cannot always adequately secure the pit and when the peach halves fall away, the entire pit may stay embedded in one of the halves. Alternatively, the pit may split in half or fragment into smaller pieces.

Successful removal of pits from cling peaches presents a considerable agricultural processing challenge. In conventional agricultural processing plants, split peach halves are visually inspected for pits or pit fragments by large numbers of inspectors standing on opposite sides of conveyors belts used to transport the peach halves. Unfortunately, the pit color closely matches the color of peach flesh. This is due in part to tendrils of peach flesh that cling to the surface of the pit. Therefore, the inspectors must rely on their visual shape recognition capabilities to recognize unacceptable product. Moreover, the inspectors often have to manually detect small "hidden" pit fragments by wiping the tip of their fingers around the cavity left in the peach by a removed pit. These inspection difficulties have previously ruled out automatically inspecting peach halves with machine vision techniques that detect visual wavelengths of light.

Even if machine vision inspection techniques were employed, the close color match between peach flesh and pits and the hidden nature of many pit fragments would render such inspection unreliable. Improving machine vision inspection reliability involves careful attention to both the camera or cameras employed and the illumination of the product being inspected. Suitable illumination typically employs a uniform, shadowless, high intensity light source to illuminate the product being inspected. Prior light sources include fluorescent lamps, incandescent bulbs, and short and long arc discharge lamps. The assignee of this application, SRC Vision, of Medford, Oreg. has used all of these sources and found them wanting in one aspect or another.

For example, FIG. 1 shows a "Brite-Lite" illumination source 10 manufactured by the assignee of this application, in which a fluorescent tube 12 is mounted at one foci of an elliptical or parabolic reflector 14 and the other foci lies in a linear inspection zone 16 on the plane of a conveyor belt 18 moving articles 20 to be inspected. A line scanning inspection camera 22 has its field of view that is co-aligned with the energy from fluorescent tube 12 focused in inspection zone 16 to maximize the amount of illumination reflected off articles 20 and received by inspection camera 22. This illumination technique produces a fairly uniform illumination inspection zone 16, but the illumination decreases near the edges of belt 18 because light illuminating the center of belt 18 propagates from any and all points along the length of fluorescent tube 12. However, because fluorescent tube 12 has a finite length and extends only five or six inches beyond the belt edges, illumination reaching points near the belt edges propagates mainly from portions of fluorescent tube 12 directly over the belt and, to a lesser extent, from any short portions that extend beyond the belt edges. Moreover, this technique is not entirely shadowless, which makes pit fragment detection difficult. Consider an article with some height, such as an apple cube lying within inspection zone 16. A point lying immediately to one side of the cube will receive light from only that portion of fluorescent tube 12 that extends in a direction away from that side of the cube. The cube itself will block the light from that portion of fluorescent tube 12 that extends in the direction of the cube. There is, however, some partial filling in of the shadow by that portion of fluorescent tube 12 that is not blocked by the cube.

To provide shadowless illumination, the light rays should ideally be parallel and perpendicular to the surface of belt 18. One way to produce this ideal illumination is to employ an illumination point source at an infinite distance. However, this technique is impractical because the illumination intensity decreases inversely with the square of the distance from the light source.

FIG. 2 shows another exemplary illumination source 30 that employs multiple incandescent lamps 32 each having an associated reflector. Illumination source 30 simulates multiple illumination point sources propagating from a significant distance, but is not very energy efficient because the illumination from each of lamps 32 is spread over a relatively large area of belt 18. Illumination uniformity is approximated by appropriately aiming lamps 32 and by adjusting their individual illumination levels. This is a labor intensive process that is prone to errors. Moreover, indiscriminate adjustment of lamp 32 illumination levels may alter their spectral wavelength distributions.

FIG. 3 shows yet another exemplary illumination source 40 that employs a pair of moderate length high-intensity discharge ("HID") tubes 42 positioned at the foci of two astigmatic cylindrical projection lenses 44. In illumination source 40, only those light rays that intersect flat back surfaces 46 of projection lenses 44 are focused on inspection zone 16 of conveyor belt 18, which renders this technique inefficient. Moreover, because the lengths of HID tubes 44 is short compared to the width of belt 18, the light rays must diverge to spread across the width of belt 18, which introduces shadowing because the angle of incidence of the light rays is not perpendicular to belt 18. Using multiple HID lamps 44 and projection lenses 44 can somewhat alleviate this problem.

What is needed, therefore, is an illumination and detection technique suitable for automatically inspecting peach halves for pits and pit fragments.

OBJECTS OF THE INVENTION

An object of this invention is, therefore to overcome the shortcomings of the prior art.

Another object of this invention is to provide an automated electro-optical means for detecting faulty articles in a low contrast ratio and low signal level environment.

A further object of this invention is to provide for the automated detection of peach pits and pit fragments in peach flesh.

Yet another object of this invention is to provide an illumination source and detector combination suitable for achieving all the objects of this invention.

A peach sorting system of this invention conveys peach halves, some of which include pits or pit fragments, on a conveyor belt past an inspection zone that is lighted by an illumination source that radiates both visible and infrared radiation. The illumination source generates numerous peaks of visible and infrared radiation over a broad spectrum. Such an illumination source is a high-pressure Indium Iodide doped high intensity discharge lamp. The radiation is reflected off a parabolic reflector and through a "soda straw" collimator to illuminated the peaches. A detector system employs line scanning visible and infrared cameras to sense visible and IR wavelength reflectance value differences existing between the peach meat and the peach pit or pit fragments. Because there is a reversal in the reflectance values between the visible and infrared wavelengths, a data subtraction technique is employed to enhance the detection contrast ratio. The data subtraction technique also cancels "glint" caused by specular reflections of the illumination source off the peaches and into the cameras.

Additional objects and advantages of this invention will be apparent from the following detailed description of preferred embodiments thereof that proceed with reference to the accompanying drawings.

BRIEF DESCRIPTION OF THE DRAWINGS

FIGS. 8 and 9 are plan and elevation views of a preferred Indium Iodine illumination source of this invention showing a parabolic reflector, parallel mirror surfaces, and a "soda straw" collimator.

FIG. 10 is a schematic pictorial view of a peach sorting system of this invention.

DETAILED DESCRIPTION OF THIS INVENTION

Figure 4:
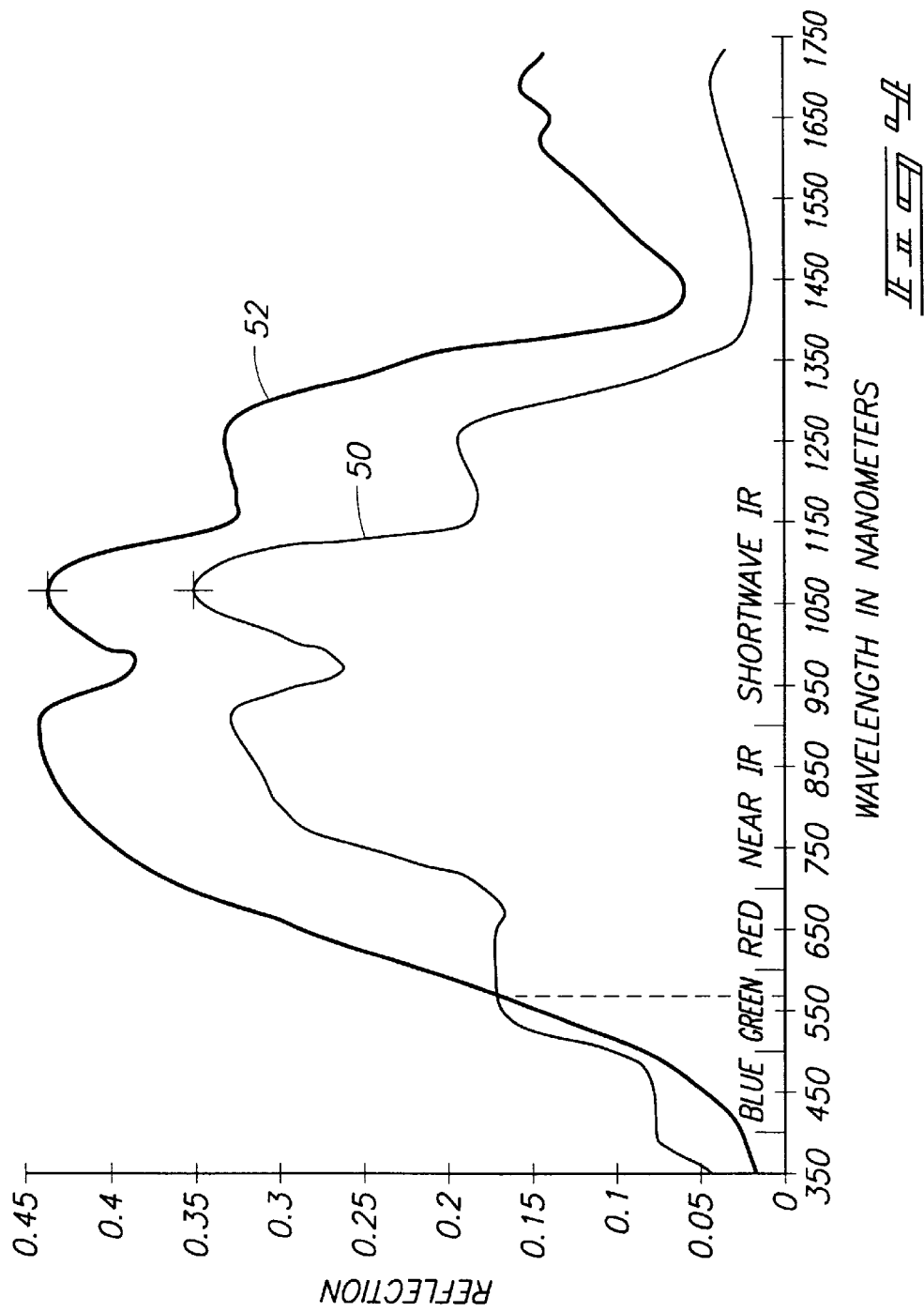
FIG. 4 is a graphical representation of the reflectance versus illumination wavelength of Chilean Cling peach flesh and peach pits.

The inventors have discovered that there is a reversal of reflectivity between peach meat and peach pits in the visible versus the infrared portions of the electromagnetic spectrum, at which wavelengths peach pits reflect significantly more energy than peach flesh. For example, FIG. 4 shows spectro-radiographic scans representing the reflectance of Chilean Cling peach flesh 50 and peach pits 52 taken at visible and infrared wavelengths ranging from 350 nanometers ("nm") to 1750 nm. Chilean peach meat 50 exhibits more reflectance in the blue visible wavelengths between 400 nm and 560 nm than does Chilean peach pits 52. However, the reflectance of flesh 50 and pits 52 reverses at about 560 nm and diverges rapidly in the infrared wavelengths above 700 nm.

Figure 5:
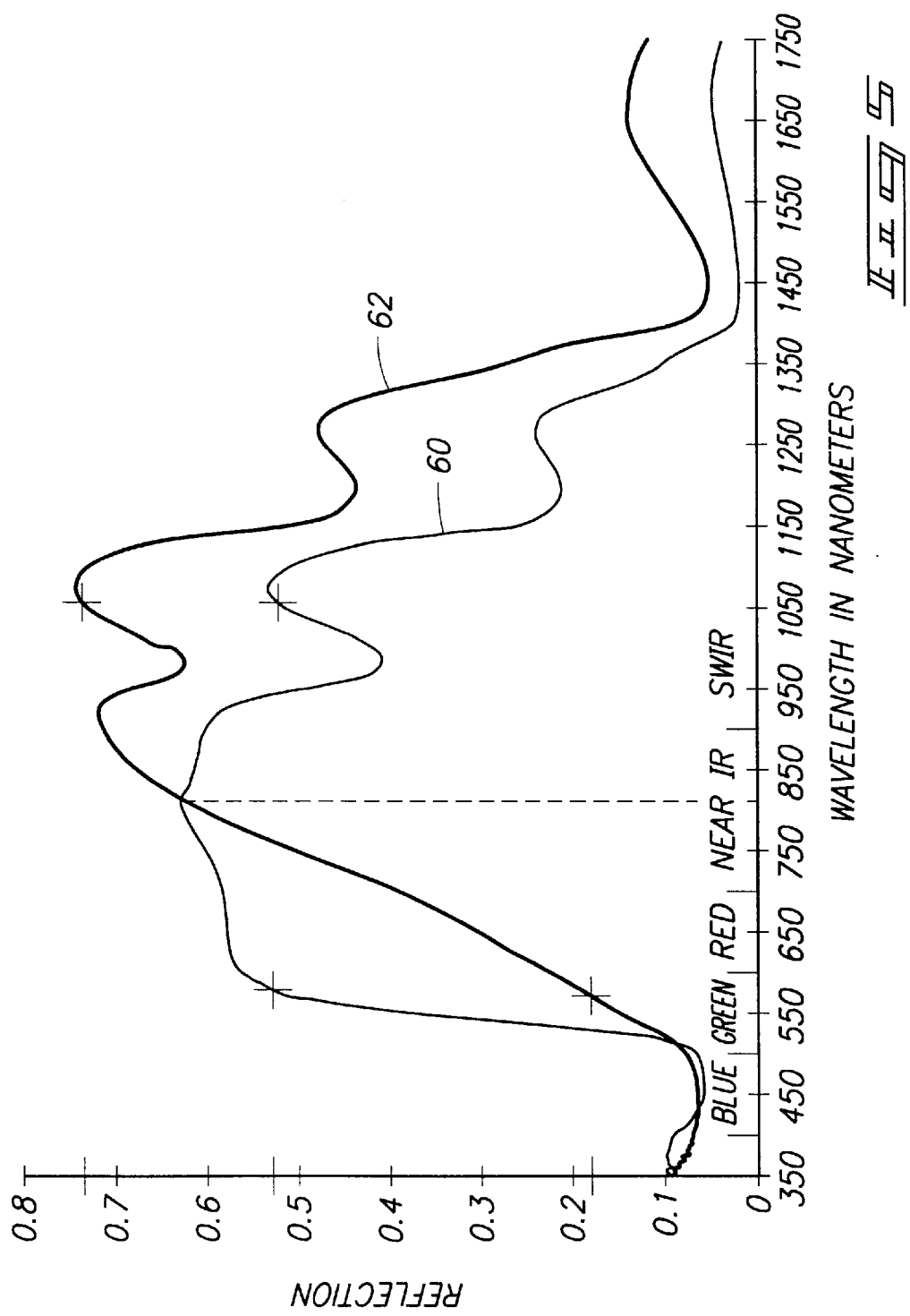
FIG. 5 is a graphical representation of the reflectance versus illumination wavelength of Australian peach flesh and peach pits.

In another example, FIG. 5 shows spectro-radiographic scans representing the reflectance of Australian peach flesh 60 and peach pits 62 taken at visible and infrared wavelengths ranging from 350 nm to 1750 nm. Australian peach meat 60 exhibits more reflectance in the green and red visible wavelengths between 510 nm and 700 nm than does Australian peach pits 62. However, the reflectance of flesh 60 and pits 62 reverses and diverges rapidly in the infrared wavelengths above 800 nm.

To exploit these reflectance differences, this invention illuminates the peach halves with a source of electromagnetic energy rich in the energy wavelengths of interest and detects the reflected visible and infrared energy with a camera or cameras that are sensitive to those wavelengths.

There are numerous illumination sources that emit energy in the visible and/or infrared portions of the electromagnetic spectrum including incandescent sources, such as hot wires. However, most of these sources emit their energy over an excessively broad portion of the spectrum and are, therefore, inefficient and insufficiently concentrated in the desired portion of the spectrum to be successfully detected by a line scanning camera. A suitable illumination source should efficiently and brightly emit all or most of its energy at the desired wavelength or wavelength ranges.

Figure 6:
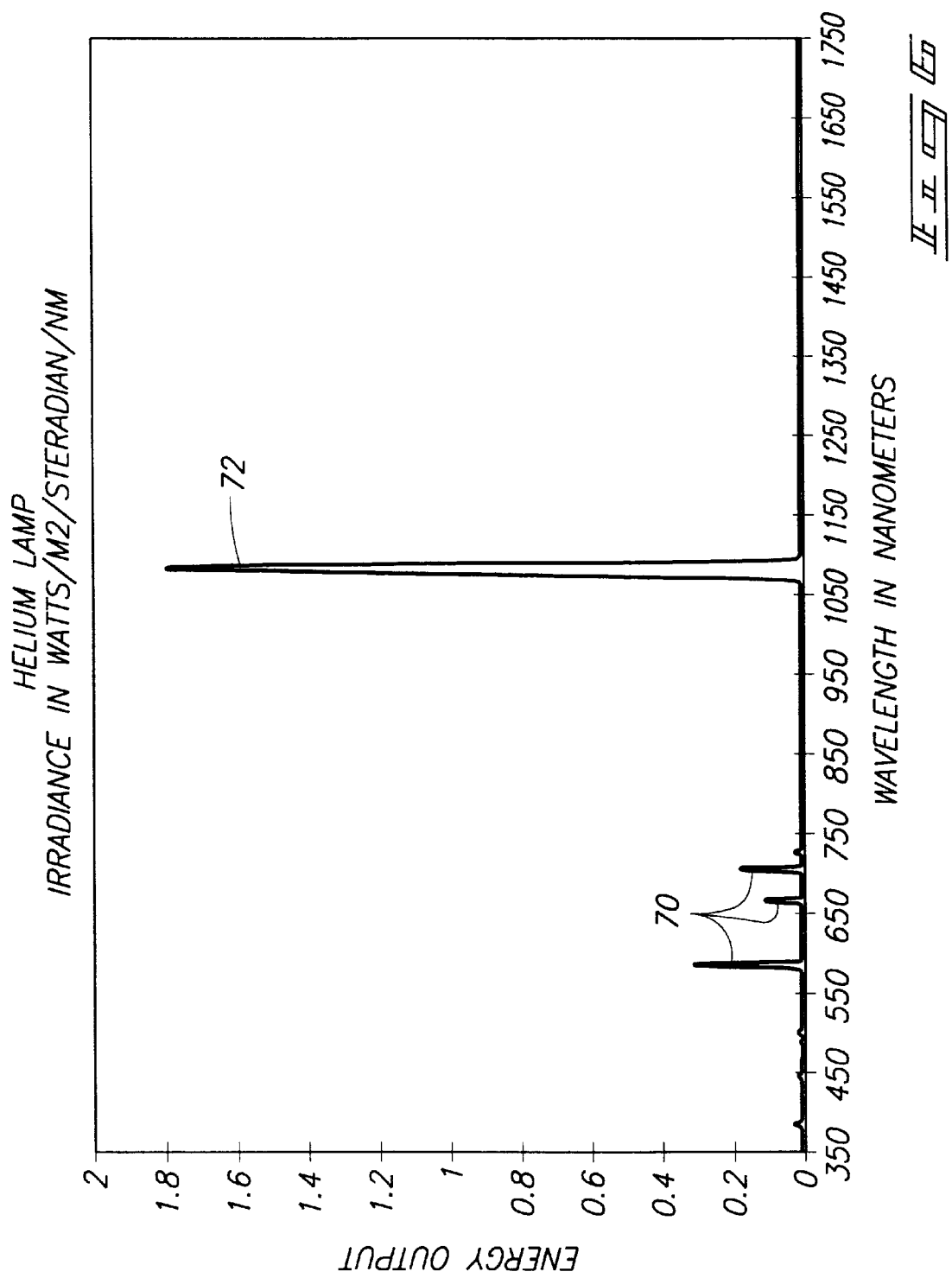
FIG. 6 is a graphical representation of the energy output versus wavelength of a Helium plasma discharge illumination source.
Figure 7:
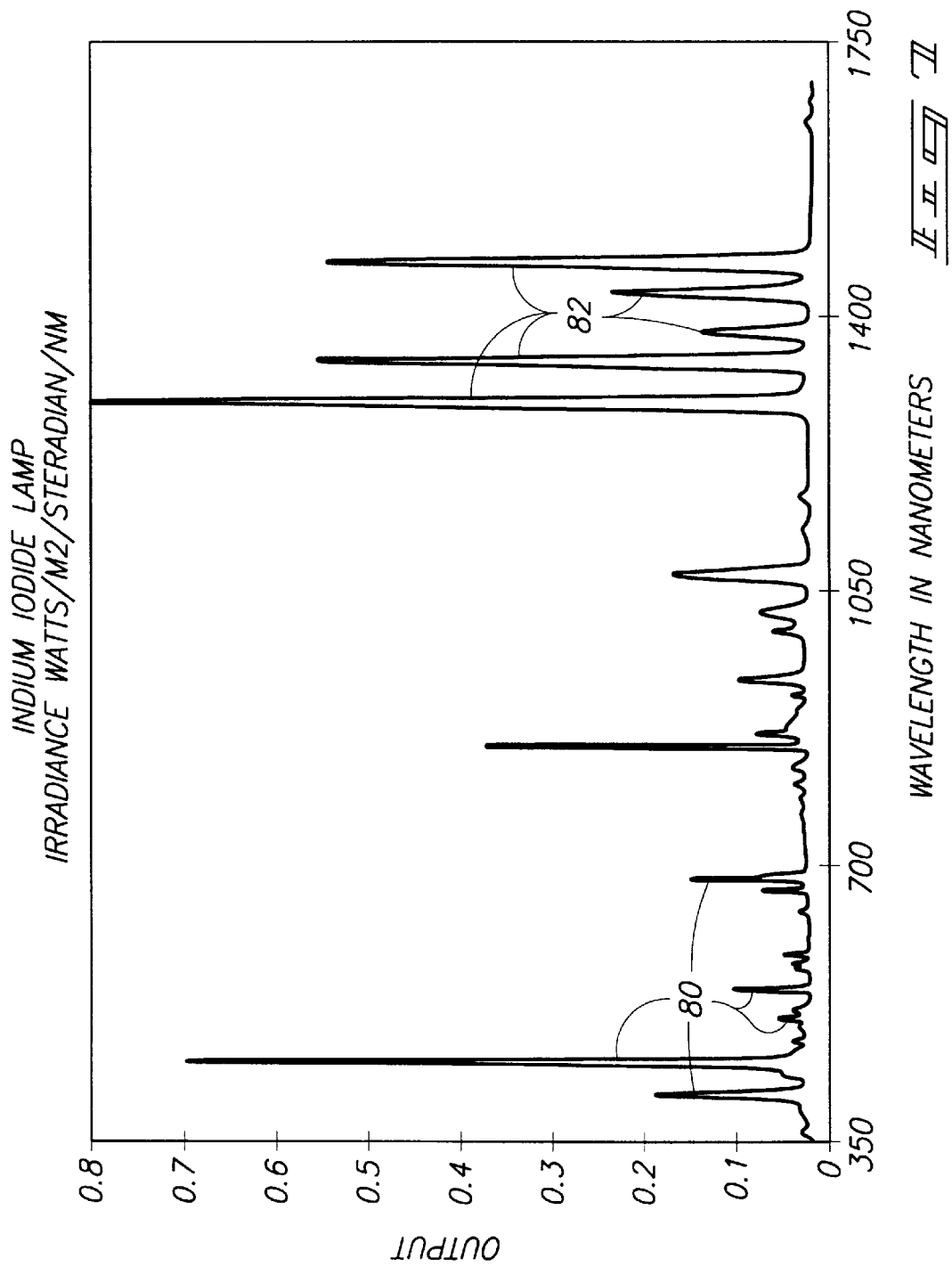
FIG. 7 is a graphical representation of the energy output versus wavelength of an Indium Iodine arc discharge illumination source.

FIGS. 6 and 7 show the spectral energy distributions of two suitable illumination sources.

In particular, FIG. 6 shows the energy output spectrum of a Helium gas filled lamp that is manufactured by the assignee of this application. The spectrum includes visible wavelength energy lines 70 and a high energy infrared line 72 at about 1,080 nm, which is a suitable wavelength for detection of Chilean or Australian peach pits or fragments of peach pits.

Likewise, FIG. 7 shows the energy output spectrum of an Indium Iodide arc discharge lamp that is manufactured by Specialty Discharge Lighting, located in Bellevue, Ohio. The spectrum includes energy in four major visible wavelength lines 80 ranging from 411 nm to 690 nm and five major infrared energy lines ranging from 1,280 nm to 1,470 nm, which are preferred wavelength ranges for detecting reflectance differences between peach meats, peach pits, and pit fragments.

In machine vision-based inspection systems, reliable detection depends on achieving suitable contrast and signal-to-noise ratios. The contrast ratio may be described as the ratio of defect (pit or fragment) reflectivity to good product (peach meat) reflectivity at a predetermined wavelength or wavelengths. As shown in FIG. 4, the contrast ratio of Chilean peach pits to peach flesh at 1,080 nm (Helium lamp) is about 0.43:0.34, or about 1.26:1. For the Indium Iodide illumination source, the contrast ratio is a weighted average of the contrast ratios computed for each of the major lines. The weighting factor for each line is proportional to the fractional portion of the overall energy in each given line. For the five lines 82 between 1,280 nm and 1,470 nm, the first line's weighting factor is about 20 percent of the total. For the first line the contrast ratio is about 0.34:0.18, or 1.89:1.

The contrast ratio at 1,080 nm (Helium lamp) of the Australian peach pit 62 to meat 60 is approximately 0.72/0.53=1.38:1, whereas at 580 nm in the visible portion of the spectrum, the contrast ratio of pit 62 to meat 60 is 0.18/0.52=0.34:1.

Clearly, the visible and infrared contrast ratios are more detectable with the Indium Iodide source than with the Helium source.

The Signal to Noise ratio may be described as the ratio signal energy (reflected light received by the camera and converted into an electronic signal) generated by the camera to the stochastic (time varying) noise energy (snow) generated by the camera. If the desired peach and pit images are obscured by snow, distinguishing between them is difficult no matter how high the contrast ratio. The amount of signal energy depends on the illuminating source intensity, the reflectivity of the object being inspected, the F-number of the camera lens, and the "exposure time" the camera has during each scan. In this invention, the Indium Iodide source provides significantly more signal energy than the Helium lamp. Even though the reflectivity of the product and defect is higher at 1080 nm, the relatively low intensity of the Helium source renders the Indium Iodide source as the preferred illumination source.

The camera stochastic noise level depends on noise generated by hole/electron pairs recombining within the photodetector array chosen and is proportional to the absolute temperature and the square root of the signal processing bandwidth. In this invention, an Indium Gallium Arsenide ("InGaAs") photodetector array is preferred because its sensitivity peaks between 1,000 nm and 1,600 nm. Suitable InGaAs photodetector arrays are available from Sensors Unlimited, Inc. of Princeton, N.J. Fortunately, in this wavelength range the quantum efficiency of the InGaAs photodetector array is very high (approaching 80 percent) and the noise is relatively low. A figure of merit that expresses the ratio of photodetector sensitivity to stochastic noise generation is referred to as Noise Equivalent Power, which is the amount of signal needed to equal the noise generated by the photodetector. For InGaAs photo detectors, the measured Noise Equivalent Power is about $5.12 \times 10^{-13}$ watts. This very low noise power means that the amount of signal energy received by the photodetector can be correspondingly low and still maintain a usable signal to noise ratio. This confirms that the Helium illumination source is a viable alternative to the Indium Iodide illumination source.

FIGS. 8 and 9 show plan and elevation views of a preferred illumination source 90 of this invention that provides uniform, intense, parallel illumination of a linear inspection zone. An HID lamp 92, having a length of about 30 cm (12 inches) and filled with a Indium Iodine gas mixture, is positioned at the focus of a cylindrical parabolic reflector 94. HID lamp 92 is oriented so that its longitudinal axis is aligned with a projection axis 96 of reflector 94. Reflector 94 is formed from polished aluminum having a protective dielectric surface coating and may be gold-plated to enhance its IR reflectivity. Illumination source 90 includes mirror-surfaced top and bottom caps 98 that are angled outwardly from lamp 92 and become parallel planar mirror surfaces after emerging from reflector 94. Top and bottom caps 98 may also be gold-plated to enhance their IR reflectivity. Substantially all the light rays propagating from HID lamp 92 are received by reflector 94 and caps 98 and are reflected generally along projection axis 96.

A "soda straw collimator" 100 comprises multiple walls 102 extending perpendicularly between top and bottom caps 98 and aligned parallel to projection axis 96. Walls 102 have diffuse surfaces and their length to pitch ratio allows only light rays that are substantially parallel to projection axis 96 to exit illumination source 90, thereby virtually eliminating any shadowing that would be detrimental to detecting peach pits or pit fragments.

In particular, consider light rays A and B, which propagate along typical paths. Light ray A emanates from the center of HID lamp 92 and reflects off reflector 94 in a direction substantially parallel to projection axis 96. However, light ray B emanates from an end of HID lamp 92 and reflects off reflector 94 in a direction that is not parallel to projection axis 96. Soda straw collimator 100 diffuses and/or absorbs all light rays B that strike walls 102 at high incident angles and passes all light rays B that strike walls 102 at zero, low, or glancing, angles of incidence.

The exit aperture of illumination source 90 may be covered with an optional protective window 104 formed from a material transmissive to visible and IR radiation.

FIG. 10 shows a peach sorting system 110 constructed in accordance with this invention. Generally, the system 110 includes: an endless conveyor belt 112 for transporting peaches 114 through an inspection zone 116; at least one, but preferably two of illumination sources 90 for illuminating peaches 114 in inspection zone 116; a detector system 118 for detecting reflected rays 120 and 121; a sorting system 122 for separating peach meat 124 from peach pit and pit fragments 126; and a control system 126 for controlling the operation of sorting system 122 based on signals from detector system 118 and a rotary shaft encoder 128 coupled to conveyor belt 112. Although peaches 114 are inspected on conveyor belt 112 in the illustrated embodiment, it will be appreciated that in-the-air (e.g., off belt) inspection or other techniques may be employed if desired.

Endless conveyor belt 112 is driven by a motorized drive roller 130 at a speed selected so that acceptable peaches 114 are projected from conveyor belt 112 along a trajectory 132 into an accept area 134, unless deflected by sorting system 122 into a reject area 136 along a trajectory 138. Preferably, conveyor belt 112 is provided with a black matte or other anti-reflective surface finish to reduce background reflections and improve the effective signal-to-noise ratio detected by detector system 118. Peaches 114 may be singulated or distributed in an essentially random fashion across the length and width of conveyor belt 112.

Figure 1:
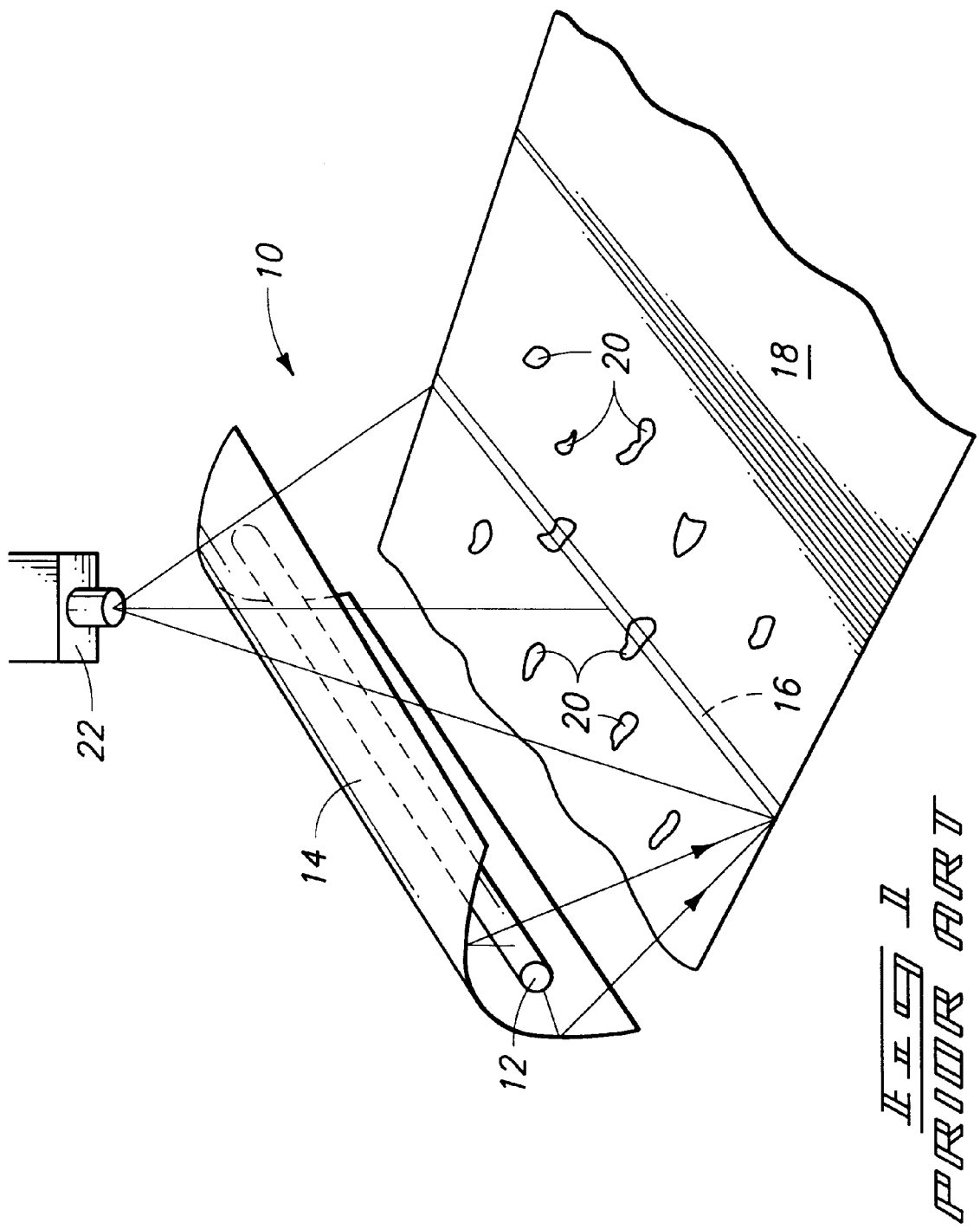
FIG. 1 is an isometric pictorial view of a prior art illumination source showing a fluorescent tube mounted at one foci of a reflector.
Figure 2:
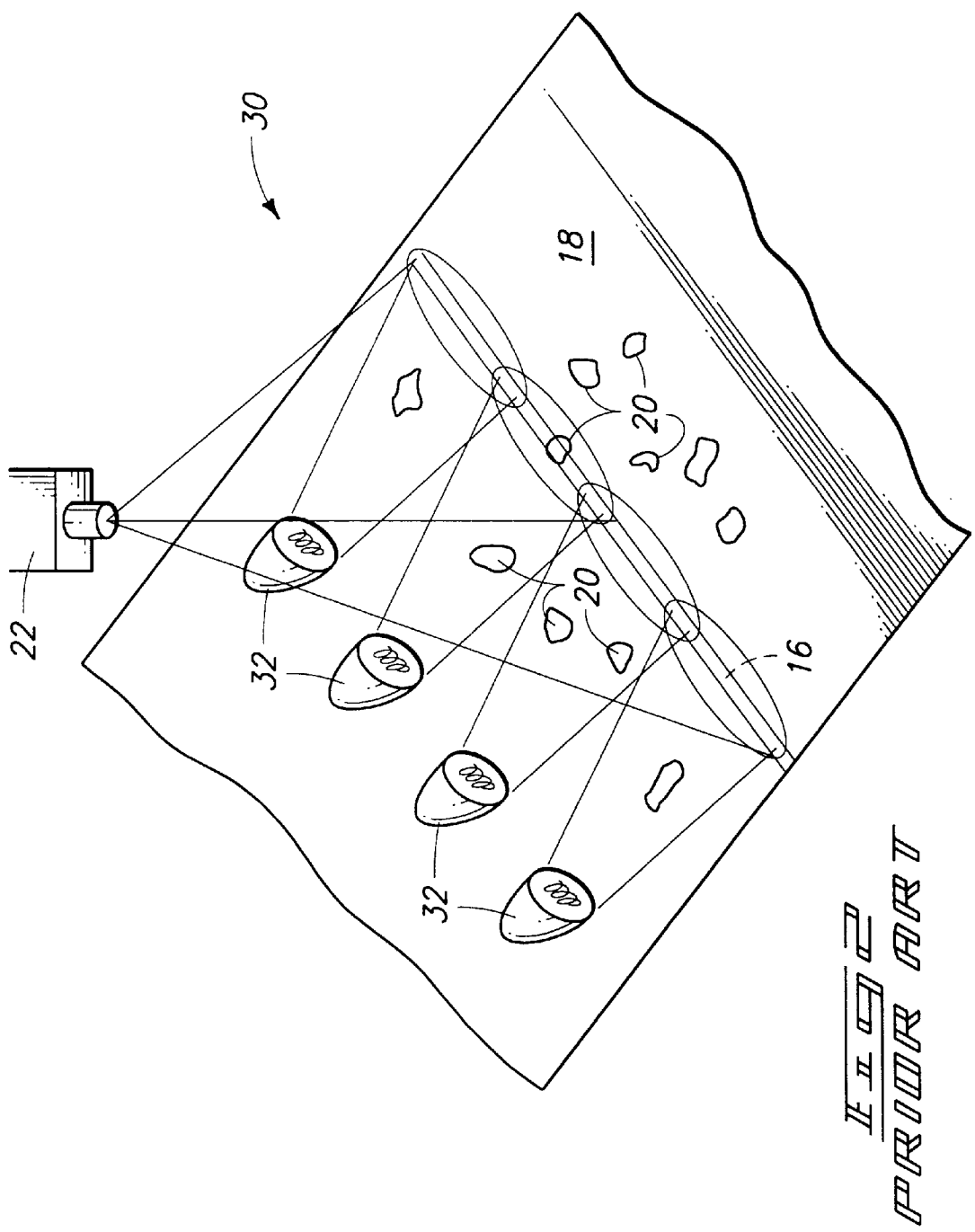
FIG. 2 is an isometric pictorial view of another prior art illumination source showing multiple incandescent light bulbs each having an associated reflector.
Figure 3:
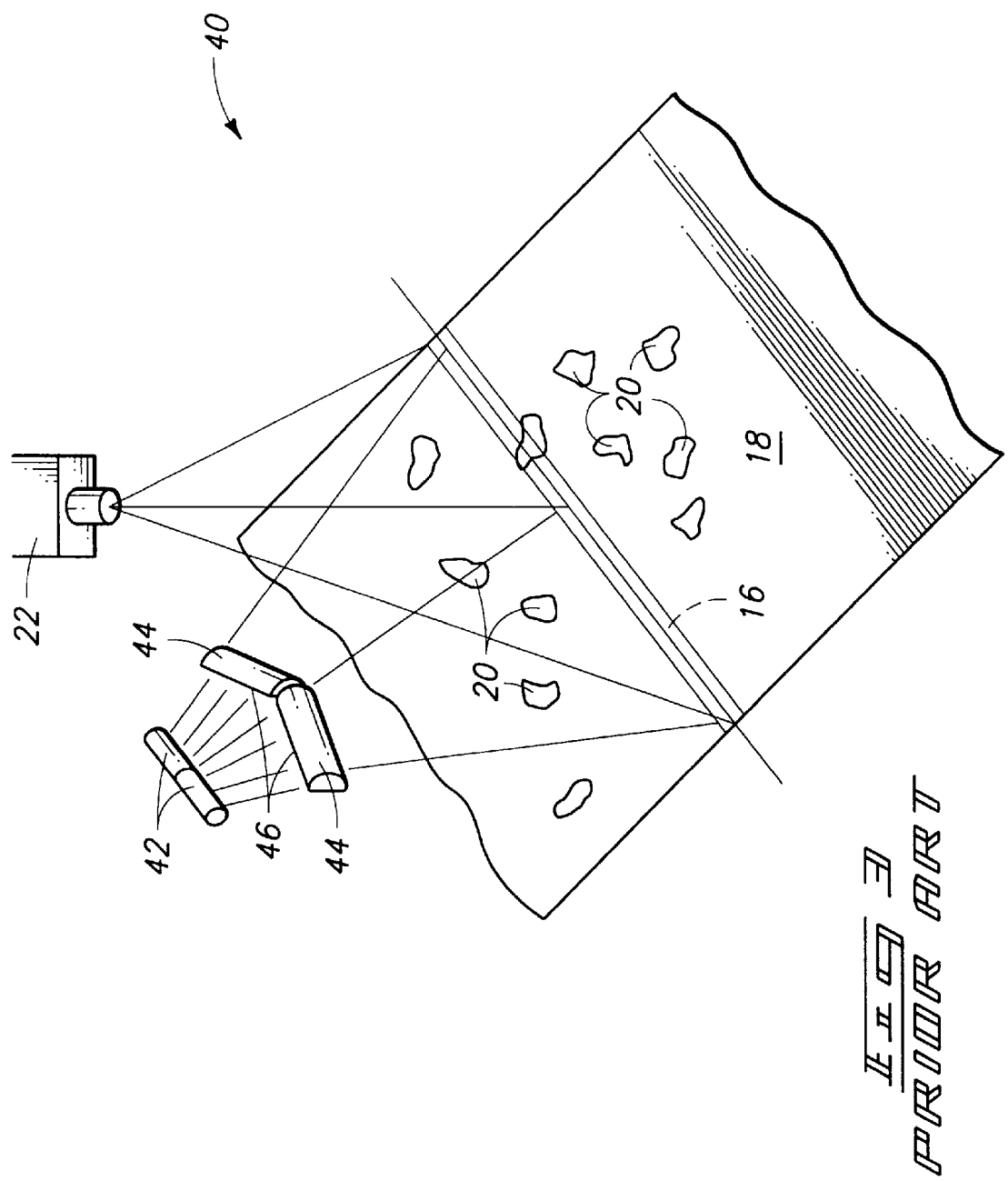
FIG. 3 is an isometric pictorial view of yet another prior art illumination source showing two moderate length HID lamps positioned at the foci of two astigmatic cylindrical lenses.

Illumination sources 90 of FIGS. 8 and 9 provide a stripe of illumination in inspection zone 116 having a substantially uniform intensity across the width of conveyor belt 112. The illumination system includes a pair of illumination sources 90 facing inwardly from opposite sides of inspection zone 116 to provide detector system 118 an unobscured view of inspection zone 116 and to reduce detection errors caused by shadowing. The particular type of HID lamp 92 employed will depend on the specific reflection characteristic under analysis as described with reference to FIGS. 6 and 7. However, Helium lamps preferably employ the prior art reflector structure shown in FIG. 1.

Detector system 118 includes a short wave infrared ("SWIR") camera 140 that is optically co-aligned with a visible camera 142. SWIR camera 140 is manufactured by the assignee of this application using Indium Gallium Arsenide detector arrays available from EG&G Judson of Montgomeryville, Pa., or by Sensors Unlimited of Princeton, N.J. Visible camera 142 is manufactured by the assignee of this application using a silicon detector array available from Thomson CSF of Paris, France. Both cameras are line scanning cameras and therefore have a linear field of view that lies across conveyor belt 112 and defines inspection zone 116. As peaches 114 passes through inspection zone 116, cameras 140 and 142 develop line-by-line video images of peaches 114 that are conveyed to control system 126 for processing.

Visible camera 142 may have 1024 pixels in its detector array whereas SWIR camera 140 may have only 512 pixels in its detector array. Therefore, when cameras 140 and 142 are optically co-aligned, two visible pixels must overlie one SWIR pixel. The two fields of view are co-aligned by means of a cold mirror 144 that reflects the visible portion of the spectrum and transmits the infrared portion of the spectrum. Alternatively, if a hot mirror is used, the transmission and reflection paths would be spectrally reversed.

In an alternative embodiment, instead of using two separate cameras and a cold (or hot) mirror, a single camera employing a dichroic beam splitter could be used to combine the visible and infrared fields of view. The assignee of this application has made such a camera by installing therein a visible and infrared dichroic beam splitter in place of a red, green, and blue dichroic beam splitter. This has the added advantage of being a more stable structure. A suitable dichroic beam splitters is available under specification drawing No. SSB-BA005-01 from Canon U.S.A., Inc., located in Irvine, Calif.

FIG. 10 further shows a detailed view of one of peaches 114 in inspection zone 116 in which reflected ray 120 is reflected from peach meat 124, and reflected ray 121 is reflected from peach pit 126 (rays 120 and 121 are actually in a combined field of view, but are shown diverged only for purposes of explanation). When reflected rays 120 and 121 are viewed by cameras 140 and 142, the resulting image consists of two adjacent pixels in visible camera 142 and one pixel in SWIR camera 140.

In an operational example, assume that the video gains of cameras 140 and 142 have been adjusted so that for a reference 100% illumination level reflected from illumination sources 90, both cameras generate a 1-volt signal. Then, with reference to FIG. 5 for Australian peaches, reflected ray 120, from peach meat 124, generates 520 mV in visible camera 142 and 520 mV in the SWIR camera 140, while reflected ray 121, from peach pit 126, generates 180 mV in visible camera 142 and 720 mV in the SWIR camera 140.

Subtracting the visible pixel values from the SWIR pixel values yields the following values. For reflected ray 120 (peach meat 124), 520 mV−520 mV=0 mV. Because video levels cannot be negative, any negative values would be set to zero. For reflected ray 121 (peach pits 126), 720 mV−180 mV=540 mV. The net result is that peach meat 124 drops out of the image and only peach pit 126 are detected. This subtraction technique drives the contrast ratio to infinity and makes peach sorting considerably easier. By adjusting the video gain of either the visible or SWIR cameras this effect can be enhanced or diminished.

Another benefit of the subtraction technique is the elimination of "Glint," which is defined as unwanted specular reflection of the light source directly into the field of view of the camera. Fresh peaches 114 are typically wet and, therefore, shiny causing reflection of at least a part of the illumination source directly into the fields of views of cameras 140 and 141. The resulting glint drives both cameras into saturation (1 volt). However, when the visible glint value is subtracted from the SWIR glint value, the result is zero. Therefore, the combined and processed images from cameras 140 and 141 do not include "Glint".

Figure 11:
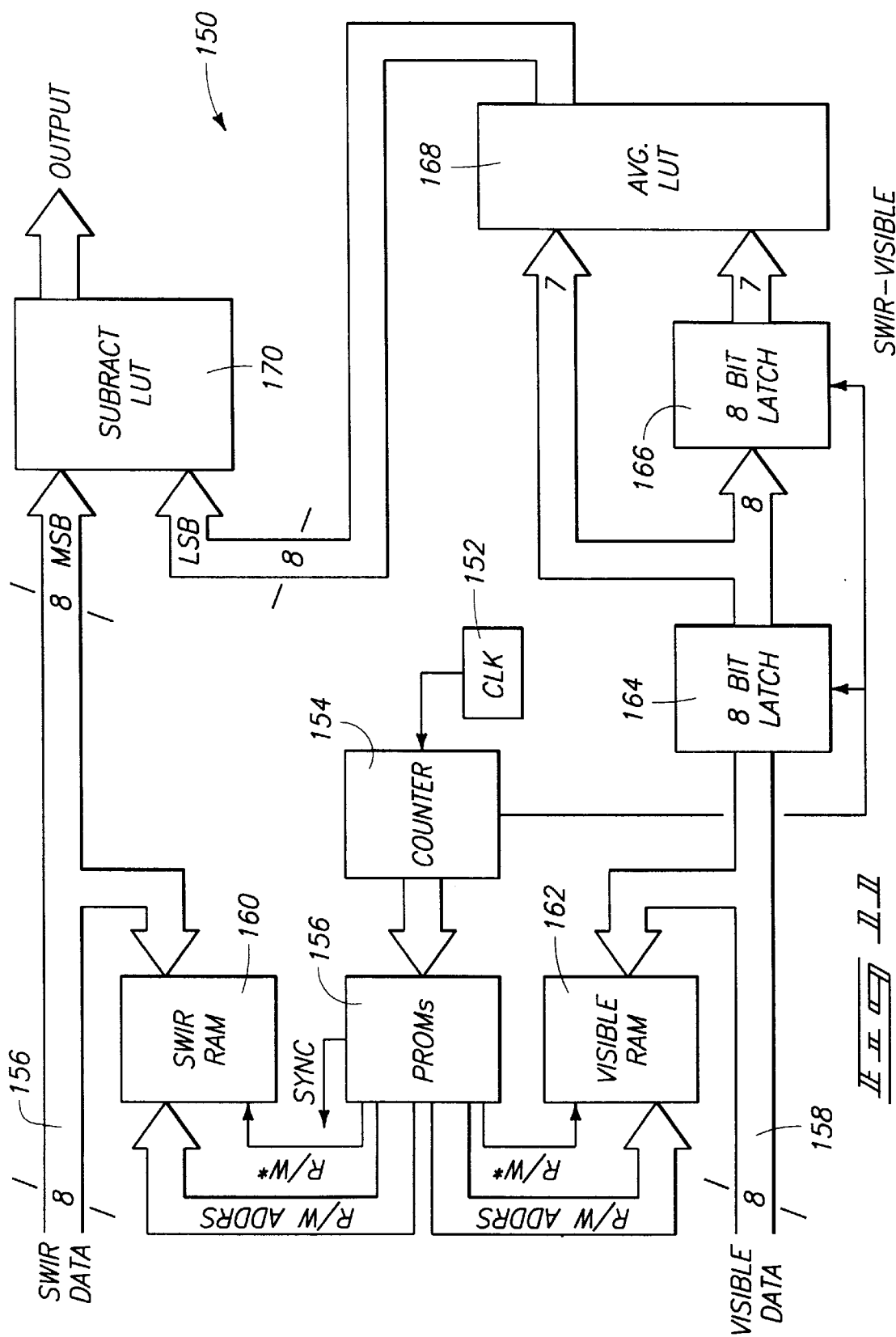
FIG. 11 is a functional block diagram of a technique for subtracting visible light values from infrared light values in accordance with this invention.

FIG. 11 shows representative circuitry that may be employed to perform the above-described subtraction. Skilled workers will understand that the subtraction technique can be carried out by any computer sufficiently fast to perform the operations in real time. FIG. 11 shows a subtraction processor 150 that carries out the subtraction technique on a pixel by pixel basis in real time without employing a computer.

Subtraction processor 150 is preferably a state machine driven by a clock 152. Clock 152 drives a counter 154, which sequentially provides addresses for a PROM 156. PROM 156 is programmed to provide all the other addresses, read/write not, sync, and latch signals required to operate the remaining circuitry. A sync signal is conveyed to cameras 140 and 142 to each scan of inspection zone 116. The resulting 8-bit data streams from cameras 140 and 142 are conveyed to subtraction processor 150 on an SWIR data bus 156 and a visible data bus 158. The SWIR and visible data is written into sequential locations of respective SWIR and visible RAMs 160 and 162 in response to "write" addresses generated by PROM 156. When the SWIR and visible data for a given scan line is stored, it is accessed and processed before starting the next scan line.

Reading visible data occurs at twice the reading rate of SWIR data because adjacent visible pixels values must be averaged to generate "pseudo visible pixels" that are subtracted from their corresponding SWIR pixel values. This would not be necessary if the SWIR and visible pixel sizes matched.

During an initial data reading operation, data from visible RAM 162 is stored in a first latch 164. During a next reading operation, the data stored in first latch 164 is transferred to a second latch 166 and a next data byte from visible RAM 162 is stored in first latch 164.

The average of A&B is (A+B)/2 which is equal to (A/2)+(B/2). For a binary digital number, A/2 may be achieved by discarding the least significant bit and shifting one bit to the right. This form of averaging is accomplished by addressing an averaging lookup table ("LUT") 168 with the seven most significant bits from first and second latches 164 and 166. Averaging LUT 168 is programmed to add the two 7-bit addresses together to complete the averaging operation.

The resultant 8-bit average number forms a least significant address byte into a subtraction LUT 170. The corresponding 8-bit SWIR pixel value forms the most significant address byte into subtraction LUT 170. Stored in each memory location of subtraction LUT 170 is the difference between the current SWIR pixel value minus the average visible pixel value. If the difference is negative, zero is stored. Data provided by subtraction LUT 170 is employed by control system 126 to control sorting system 122 such that acceptable peaches are separated from unacceptable peaches.

Because the pixel values being read from RAM 160 are determined by the RAM address, PROM 156 can be programmed to average non-adjacent pixel values. This may be useful if there is some kind of optical non-linearity between cameras 140 and 142. For example, pixel 250 of SWIR camera 140 may not exactly overlay pixels 500 and 501 of visible camera 142, but may instead overlay a small part of pixel 506, all of 507, and most of 508. In this example, pixels 507 and 508 could be averaged and then subtracted from SWIR pixel 250.

Moreover, because SWIR camera 140 employs an InGaAs detector array, and because the technology for making this tertiary material is not well developed, it is difficult to fabricate large InGaAs arrays with flawless pixels. Therefore, most InGaAs detector arrays include some dead pixels. Fortunately, PROM 156 can be programmed to blank out these dead pixels by substituting adjacent good pixel values into the time slots normally allotted to the dead pixels.

EXPERIMENTAL RESULTS

FIGS. 12 to 17 illustrate the imaging performance of an SWIR camera employing a 128 by 128 pixel InGaAs photodetector array while viewing a peach peaches illuminated by illumination source 90. The effects of visible camera 142 and subtraction processor 150 are not shown in FIGS. 12 to 17.

Figure 12:
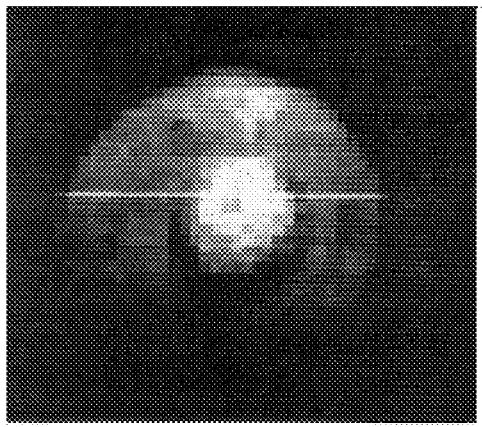
FIGS. 12 to 17 are photographs representing peach half images and measured sectional reflectance values taken under three sets of experimental conditions to evaluate the infrared detection performance of this invention.

FIG. 12 is a Polaroid photograph taken of a television monitor displaying a two-dimensionally image generated from the video output of the SWIR camera viewing a peach with an embedded pit. The peach was prepared by splitting it with a knife and immersing it in a warm 12 percent sodium hydroxide solution for 30 seconds. This preparation removes a portion of the peach flesh tendrils attached to the pit and diminishes chlorophyll effect reflectance from the peach meat. The horizontal white line traversing the peach and pit has been superimposed on the television monitor by a Tektronix waveform measurement system to indicate which displayed scan line is being measured by the waveform measurement system. FIG. 12 clearly shows that the pit is substantially brighter that the surrounding peach flesh.

Figure 13:
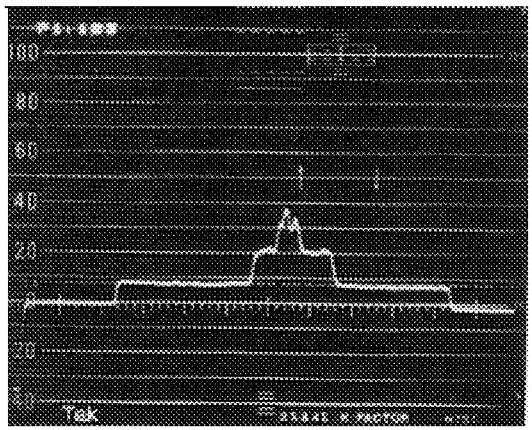

FIG. 13 shows the resulting measurement waveform displayed on the Tektronix waveform measurement system. The centrally located 38 IRE unit waveform blip representing the pit sits atop a 20 IRE unit plateau representing the peach flesh. The black background is at a 7.5 IRE unit level. The pit to meat contrast ratio ranges from about 1.7:1 and 2.4:1.

Figure 14:
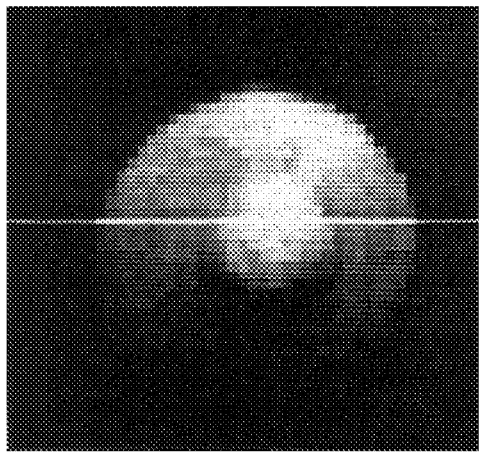
Figure 15:
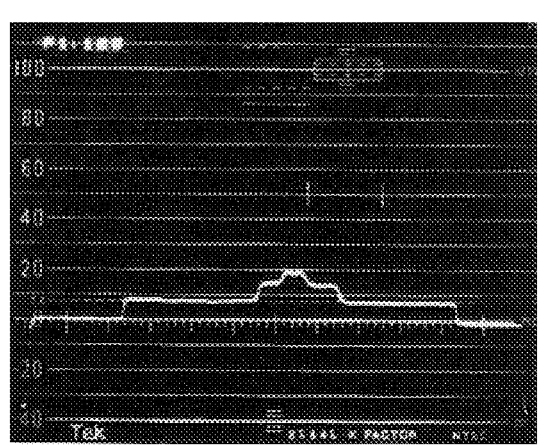

FIGS. 14 and 15 are comparable television and measurement monitor photographs taken with a Helium low pressure lamp substituted for the Indium Iodine HID lamp. In this case, the pit reflectance peaks at 20 IRE units and the peach flesh reflectance is at about 15 IRE units. As before, the black background remains at 7.5 IRE units. The contrast ratio ranges from 1.4:1 to 1.66:1.

Figure 16:
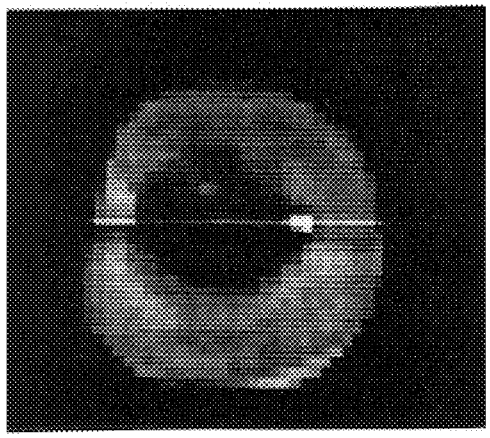
Figure 17:
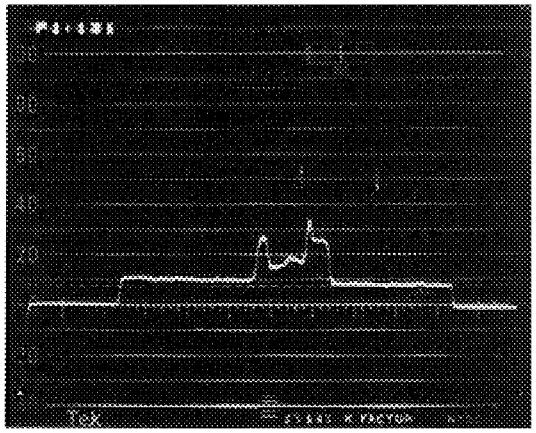

FIGS. 16 and 17 show the ability of the system of FIGS. 12 and 13 to detect small pit fragments. These results are particularly dispositive because the fragment is embedded within the pit cavity wall and in the peach flesh, a condition heretofore detected manually. The dark area in the center of the peach half represents the cavity left by the removal of the pit, and the bright spot on the right edge of the cavity represents the pit fragment. In FIG. 17, the sharp rightmost pulse on the oscilloscope trace indicates the location of the pit fragment.

It will be obvious to those having skill in the art that many changes may be made to the details of the above-described embodiment of this invention without departing from the underlying principles thereof. Accordingly, it will be appreciated that this invention is also applicable to article inspection and detection applications other than those found in peach inspection applications. The scope of the present invention should, therefore, be determined only by the following claims.

We claim:

1. An article sorting system that conveys the articles on a conveyor belt and past an inspection zone, comprising:
   an illumination source emitting visible and infrared radiation for illuminating the articles in the inspection zone; and wherein the illumination source includes at least one high-intensity discharge lamp that is filled with a gas including at least one of Helium and Indium Iodide;
   a detector system for sensing the visible and infrared radiation reflected from the articles in the inspection zone and generating visible data and infrared data;
   a subtraction processor determining a difference between the visible data and the infrared data to provide article sorting data;
   a sorter responsive to the sorting data for separating the articles into acceptable articles and unacceptable articles.

2. The system of claim 1 in which the acceptable articles include peaches, and the unacceptable articles include at least one of peach pits and pit fragments.

3. The system of claim 1 in which the articles include peach meat and peach pit material, the visible data include visible meat data and infrared meat data, and the infrared data include visible pit material data and infrared pit material data, and in which the subtraction processor subtracts the visible meat data from the infrared meat data and subtracts the visible pit material data from the infrared pit material data to provide net meat data and net pit material data that are employed by the sorter to classify articles including peach pit material as unacceptable articles.

4. The system of claim 1 in which the articles include wet peaches that cause visible and infrared specular reflections of the illumination source into the detector system, and in which the subtraction processor subtracts visible specular reflections from the infrared specular reflections to effectively reduce detection of the visible and infrared specular reflections.

5. The system of claim 1 in which the subtraction processor is implemented as a computer program.

6. An article sorting system that conveys the articles on a conveyor belt and past an inspection zone, comprising:
   an illumination source emitting visible and infrared radiation for illuminating the articles in the inspection zone;
   a detector system for sensing the visible and infrared radiation reflected from the articles in the inspection zone and generating visible data and infrared data;
   a subtraction processor determining a difference between the visible data and the infrared data to provide article sorting data;
   a sorter responsive to the sorting data for separating the articles into acceptable articles and unacceptable articles; and wherein
   the illumination source includes at least one high-intensity discharge lamp that emits the visible and infrared radiation, which radiation reflects off a reflector and through a collimator to illuminate the inspection zone.

7. The system of claim 6 in which the reflector includes a cylindrical parabolic section having a focus and a projection axis and in which the high-intensity discharge lamp is positioned at the focus and aligned with the projection axis.

8. The system of claim 6 in which the illumination source has top and bottom caps and a projection axis and the collimator includes multiple substantially parallel walls extending between the top and bottom caps and aligned substantially parallel to the projection axis.

9. An article sorting system that conveys the articles on a conveyor belt and past an inspection zone, comprising:
   an illumination source emitting visible and infrared radiation for illuminating the articles in the inspection zone;
   a detector system for sensing the visible and infrared radiation reflected from the articles in the inspection zone and generating visible data and infrared data;
   a subtraction processor determining a difference between the visible data and the infrared data to provide article sorting data;
   a sorter responsive to the sorting data for separating the articles into acceptable articles and unacceptable articles; and wherein
   the detector system senses the visible radiation with a line scanning Silicon detector array-based camera.

10. An article sorting system that conveys the articles on a conveyor belt and past an inspection zone, comprising:
    an illumination source emitting visible and infrared radiation for illuminating the articles in the inspection zone;
    a detector system for sensing the visible and infrared radiation reflected from the articles in the inspection zone and generating visible data and infrared data;
    a subtraction processor determining a difference between the visible data and the infrared data to provide article sorting data;
    a sorter responsive to the sorting data for separating the articles into acceptable articles and unacceptable articles; and wherein
    the detector system senses the infrared radiation with a line scanning InGaAs detector array-based camera.

11. An article sorting system that conveys the articles on a conveyor belt and past an inspection zone, comprising:
    an illumination source emitting visible and infrared radiation for illuminating the articles in the inspection zone;
    a detector system for sensing the visible and infrared radiation reflected from the articles in the inspection zone and generating visible data and infrared data;
    a subtraction processor determining a difference between the visible data and the infrared data to provide article sorting data;
    a sorter responsive to the sorting data for separating the articles into acceptable articles and unacceptable articles; and wherein
    the detector system senses the visible and infrared radiation with separate visible- and infrared-sensitive cameras that are co-aligned by a cold mirror or a hot mirror to view the inspection zone.

12. A method of sorting articles by conveying the articles on a conveyor belt and past an inspection zone, comprising:
    illuminating the articles in the inspection zone with a source of visible and infrared radiation;
    sensing the visible and infrared radiation reflected from the articles in the inspection zone and generating visible data and infrared data;
    processing a difference between the visible data and the infrared data to provide article sorting data;
    separating the articles into acceptable articles and unacceptable articles in response to the sorting data; and wherein
    the illuminating includes providing at least one high-intensity discharge lamp that is filled with a gas including at least one of Helium and Indium Iodide.

13. The method of claim 12 in which the acceptable articles include peaches, and the unacceptable articles include at least one of peach pits and pit fragments.

14. The method of claim 12 in which the articles include peach meat and peach pit material, the visible data include visible meat data and infrared meat data, and the infrared data include visible pit material data and infrared pit material data, and in which the processing includes: subtracting the visible meat data from the infrared meat data, or vice versa; subtracting the visible pit material data from the infrared pit material data, or vice versa; and providing net meat data and net pit material data that are employed by the separating step for classifying articles including peach pit material as unacceptable articles.

15. The method of claim 12 in which the articles include wet peaches that cause visible and infrared specular reflections of the illumination source into the detector system, and in which the processing includes subtracting the visible specular reflections from the infrared specular reflections to effectively reduce detection of the visible and infrared specular reflections.

16. The method of claim 12 in which the processing is carried out by a computer program.

17. A method of sorting articles by conveying the articles on a conveyor belt and past an inspection zone, comprising:
    illuminating the articles in the inspection zone with a source of visible and infrared radiation;
    sensing the visible and infrared radiation reflected from the articles in the inspection zone and generating visible data and infrared data;
    processing a difference between the visible data and the infrared data to provide article sorting data;
    separating the articles into acceptable articles and unacceptable articles in response to the sorting data; and wherein
    the illuminating includes providing at least one high-intensity discharge lamp for emitting the visible and infrared radiation, reflecting the radiation off a reflector, and collimating the reflected radiation to illuminate the inspection zone.

18. A method of sorting articles by conveying the articles on a conveyor belt and past an inspection zone, comprising:
    illuminating the articles in the inspection zone with a source of visible and infrared radiation;
    sensing the visible and infrared radiation reflected from the articles in the inspection zone and generating visible data and infrared data;
    processing a difference between the visible data and the infrared data to provide article sorting data;
    separating the articles into acceptable articles and unacceptable articles in response to the sorting data; and wherein
    the sensing includes sensing the visible and infrared radiation with a red, green, and infrared dichroic beam splitter-based camera.

19. A method of sorting articles by conveying the articles on a conveyor belt and past an inspection zone, comprising:

illuminating the articles in the inspection zone with a source of visible and infrared radiation;

sensing the visible and infrared radiation reflected from the articles in the inspection zone and generating visible data and infrared data;

processing a difference between the visible data and the infrared data to provide article sorting data;

separating the articles into acceptable articles and unacceptable articles in response to the sorting data; and wherein the sensing includes sensing the visible radiation with a line scanning Silicon detector array-based camera.

20. A method of sorting articles by conveying the articles on a conveyor belt and past an inspection zone, comprising:

illuminating the articles in the inspection zone with a source of visible and infrared radiation;

sensing the visible and infrared radiation reflected from the articles in the inspection zone and generating visible data and infrared data;

processing a difference between the visible data and the infrared data to provide article sorting data;

separating the articles into acceptable articles and unacceptable articles in response to the sorting data; and wherein the sensing includes sensing the infrared radiation with a line scanning InGaAs detector array-based camera.

* * * * *